United States Patent [19]

Kristinsson et al.

[11] 4,254,133
[45] Mar. 3, 1981

[54] COMBATTING ECTOPARASITES WITH PHENYLAMINOALKYL-2-IMIDAZOLINE COMPOUNDS

[75] Inventors: Haukur Kristinsson, Bottmingen; Walter Traber, Reinach, both of Switzerland

[73] Assignee: Ciba-Geigy Corporation, Ardsley, N.Y.

[21] Appl. No.: 42,822

[22] Filed: May 29, 1979

Related U.S. Application Data

[63] Continuation-in-part of Ser. No. 850,444, Nov. 10, 1977, abandoned.

[30] Foreign Application Priority Data

Nov. 16, 1976 [CH] Switzerland .................. 14401/76
Nov. 16, 1976 [CH] Switzerland .................. 14402/76
Oct. 11, 1977 [CH] Switzerland .................. 12390/77

[51] Int. Cl.³ .......................................... A01N 43/50
[52] U.S. Cl. .............................. 424/273 R; 548/353
[58] Field of Search .................... 548/353; 424/273 R

[56] References Cited

U.S. PATENT DOCUMENTS 4,000,079  12/1976  Rasp et al. ..................... 548/353

FOREIGN PATENT DOCUMENTS 563673  9/1958  Canada ........................... 548/353
51-106739  9/1976  Japan .
1174349  12/1969  United Kingdom ............. 548/353

*Primary Examiner*—Allen J. Robinson
*Attorney, Agent, or Firm*—Frederick H. Rabin

[57] ABSTRACT

Compositions containing active substances of the formula

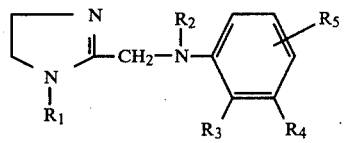

wherein $R_1$ and $R_2$, each independently of the other, represent hydrogen or alkyl of 1 to 10 carbon atoms, $R_3$ and $R_4$, each independently of the other, represent alkyl of 1 to 5 carbon atoms or halogen, preferably chlorine, and $R_5$ represents hydrogen, alkyl of 1 to 5 carbon atoms or halogen, or an acid addition salt thereof for combating ectoparasites.

4 Claims, No Drawings

COMBATTING ECTOPARASITES WITH PHENYLAMINOALKYL-2-IMIDAZOLINE COMPOUNDS

CROSS REFERENCE TO RELATED APPLICATION

This is a continuation-in-part of application Ser. No. 850,444 filed on Nov. 10, 1977 now abandoned.

The present invention relates to compositions for controlling ectoparasites and to a method of controlling ectoparasites, in particular mites and ticks, which comprises the use of said compositions.

The compositions of the present invention contain, as active component, at least one compound of the formula I

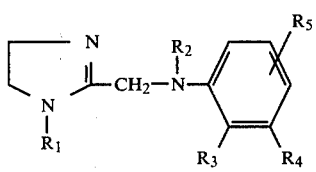

wherein
$R_1$ and $R_2$, each independently of the other, represent hydrogen or alkyl of 1 to 10 carbon atoms,
$R_3$ and $R_4$, each independently of the other, represent alkyl of 1 to 5 carbon atoms or halogen, preferably chlorine, and
$R_5$ represents hydrogen, alkyl of 1 to 5 carbon atoms or halogen,
or an acid addition salt thereof.

By alkyl groups within the scope of formula I are meant both straight chain and branched alkyl groups, for example methyl, ethyl, and the isomers of the propyl, butyl, pentyl, hexyl, heptyl, octyl, nonyl and decyl groups. Halogen is to be understood as meaning fluorine, bromine, iodine and, preferably, chlorine.

The compounds of the formula I can be converted into their acid addition salts by methods which are known per se. Preferred acid addition salts are the hydrochlorides. In addition to hydrochloric acid suitable acids for the salt formation are for example: hydrobromic acid, hydriodic acid, sulfuric acid, phosphoric acid, nitric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid and salicyclic acid.

Some of the compounds falling within the scope of the formula I are known. These compounds are disclosed as pharmaceutically active in British Pat. No. 1,174,349. Furthermore, Japanese published Pat. No. 51-106739 discloses compounds of the following general formula as active ingredients of insecticidal and acaricidal formulations:

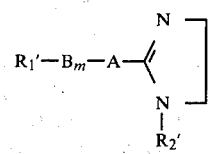

wherein A represents lower alkylene or lower alkenylene, B represents an oxygen or a sulfur atom, the NH or NCH$_3$ group, $R_1'$ represents phenyl, thienyl or naphthyl, each of which is unsubstituted or substituted by 1 to 3 halogen atoms, nitro, lower alkyl or haloalkyl and $R_2'$ represents hydrogen or lower alkyl and m is 0 or 1.

The present invention is based on the observation that the compounds of the formula I possess valuable ectoparasiticidal, especially acaricidal, properties. It has been found that the compounds of the formula I are significantly superior in respect of their acaricidal action to the individual compounds specifically described in the Japanese patent specification referred to above.

The compounds of the formula I can be obtained by methods which are known per se, for example in accordance with the syntheses illustrated by the following formulae:

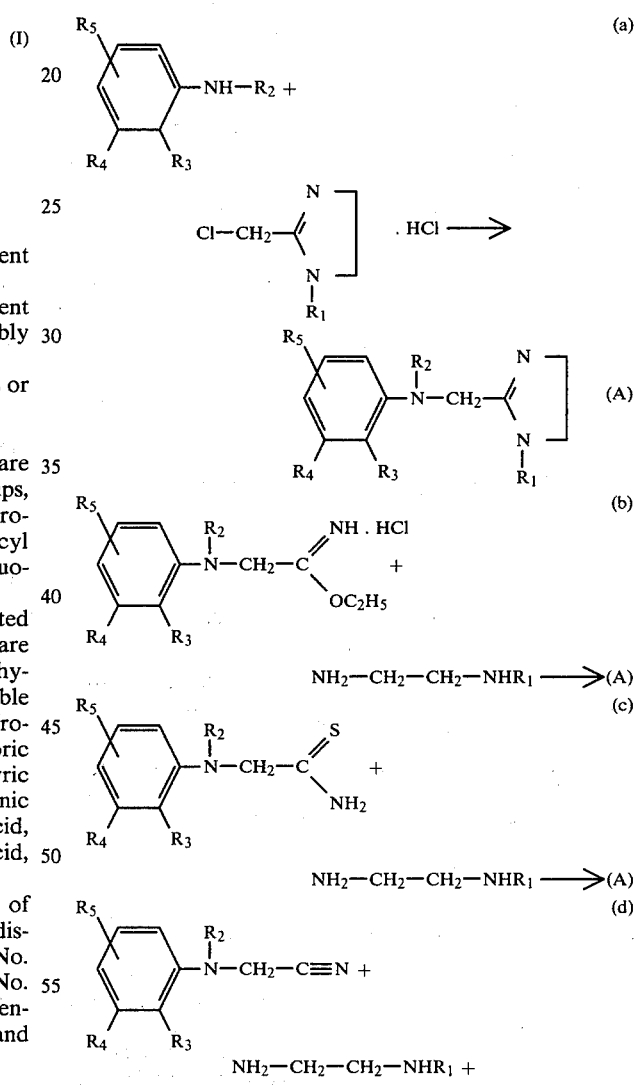

The processes are carried out in the temperature range between 40° and 180° C. and in the presence of anhydrous solvents or also without solvents. Examples of suitable solvents are: methanol, ethanol, propanol, butanol, xylene and dichlorobenzene.

The above syntheses are described in the following publications:

U.S. Pat. No. 2,252,753; Helv. Chimica Acta 33, 1386 (1950); U.S. Pat. No. 2,252,721; and British Pat. No. 1,174,349.

The individual starting materials and their manufacture are known from the following publications:

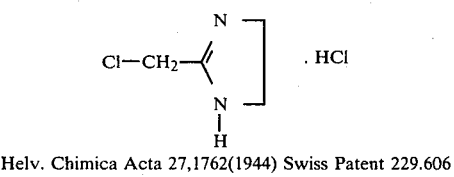

Helv. Chimica Acta 27,1762(1944) Swiss Patent 229.606

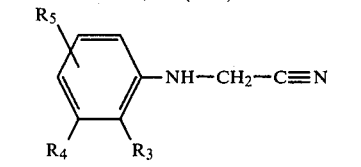

Helv. Chimica Acta 37,166 (1954)

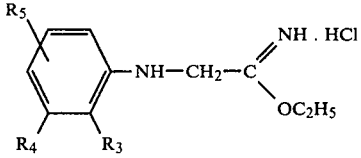

U.S. Pat. No. 2.252.721

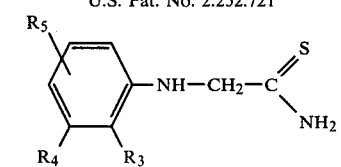

The following Examples serve to illustrate the manufacture of the compounds of the formula I:

EXAMPLE 1

(Method a)

2-(2',3'-Dimethylphenylaminomethyl)-2-imidazoline hydrochloride 31 g of 2-chloromethyl-2-imidazoline hydrochloride and 48.4 g of 2,3-dimethylaniline are refluxed for 5 hours in 65 ml of absolute ethanol. After cooling, the crystallised substance is collected by suction and recrystallised from water, affording 36 g (77% yield) of the final product with a melting point of 242° C.

EXAMPLE 2

(Method d)

2-(2',3'-Dimethylphenylaminomethyl)-2-imidazoline

A mixture of 26.4 g of 2,3-dimethylphenylacetonitrile and 39.4 g of ethylenediamine toluenesulfonate is heated to 140° C. until the evolution of ammonia ceases. Then 150 ml of 15% aqueous sodium hydroxide are added to the oily reaction product, which is extracted with three 100 ml portions of methylene chloride. The combined methylene chloride extracts are washed with water, dried over sodium sulfate and filtered. The solvent is distilled off and the residual dark oil is distilled in vacuo, affording 13.6 g (39.4% of theory) of 2-(2',2'-dimethylphenylaminomethyl)-2-imidazoline in the form of an oil with a boiling point of 154°–160° C./0.2 torr. On standing, this oil solidifies to crystals with a melting point of 80°–82° C.

The following new compounds have been prepared by procedures analogous to those described in the foregoing Examples and to the other indicated methods:

| No. | $R_1$ | $R_2$ | $R_3$ | $R_4$ | $R_5$ | salt | melting point in °C. |
|---|---|---|---|---|---|---|---|
| 1 | H | H | $CH_3$ | $CH_3$ | H | HCl | 242 |
| 2 | H | H | Cl | Cl | H | HCl | 260 |
| 3 | H | H | $CH_3$ | $CH_3$ | 6-$CH_3$ | HCl | 215 |
| 4 | $CH_3$ | H | $CH_3$ | $CH_3$ | H | HCl | 190–192 |
| 5 | $CH_3$ | $CH_3$ | $CH_3$ | $CH_3$ | H | HCl | 183–184 |
| 6 | $CH_3$ | H | Cl | Cl | H | HCl | 226–227 |
| 7 | $CH_3$ | $CH_3$ | Cl | Cl | H | HCl | |
| 8 | $CH_3$ | H | $CH_3$ | Cl | H | HCl | 212–214 |
| 9 | $CH_3$ | $CH_3$ | $CH_3$ | Cl | H | HCl | |
| 10 | H | $CH_3$ | $CH_3$ | $CH_3$ | H | HCl | 182–183 |
| 11 | H | H | $CH_3$ | $CH_3$ | H | — | 80–82 |

The novel compounds of the formula I also constitute an object of the present invention.

The compounds of the formula I as such or as constituents of the compositions of the invention possess valuable ectoparasiticidal properties. They are suitable in particular for controlling mites (Acarina), preferably parasitic ticks (Ixodidae). This applies to all stages of monoxenous and heteroxenous tick species and to the inhibition of oviposition, that is to say both to strains which are normally sensitive and those which are resistant to compounds such as phosphates, carbamates and other already known acaricides.

In addition, these compounds have a pronounced detaching effect, which is of particular importance for the treatment of host animals which are already infested with ticks (e.g. cattle or rabbits). The detaching effect commences directly after application of the active substance, as a consequence of which the ticks are prevented from continuing to feed on the host by sucking blood from it. In the course of the treatment they become detached from the host animal, which is ultimately completely freed from the pests.

Preferred compounds of the present invention are those of the formula I wherein the substituent at the phenyl ring, $R_5$, represents hydrogen, whilst $R_3$ and $R_4$, each independently of the other, are as defined for formula I.

The following compounds are distinguished by excellent acaricidal action:

2-(2',3'-dimethylanilinomethyl)-2-imidazoline hydrochloride 2-(2',3'-dichloroanilinomethyl)-2-imidazoline hydrochloride.

EXAMPLE 3

Test of the action against ticks: inhibition of oviposition

The test organisms are fully gorged females of the cattle tick, *Boophilus microplus*. 10 ticks of a resistant strain and 10 ticks of a normally sensitive strain are treated at each concentration. The ticks are dipped briefly into aqueous emulsions or aqueous solutions of the salts of the compounds to be examined. They are affixed to plates covered with double adhesive tape and stored in a climatically controlled room under constant conditions. Evaluation is made after three weeks. Total inhibiton of the deposition of fertile eggs is ascertained.

The inhibitory action of the substances is expressed as the minimum substance concentration in ppm for 100% action against normally sensitive and resistant adult female ticks.

| Compound | Results Minimum concentration in ppm at 100% inhibitory action | |
|---|---|---|
| | ♀ sensitive | ♀ resistant |
| (1) 2-(2',3'-dimethylanilino-methyl)-2-imidazoline-hydrochloride | 50 | 50 |
| (2) 2-(2',3'-dichloroanilino-methyl)-2-imidazoline-hydrochloride | 50 | 50 |
| Comparison | | |
| 2-(3,4-dichlorophenylimino)-N-n-butyl-pyrrolidine ("Bimarit") | 1000 | 1000 |
| rit">1000 methyl-thiazoline (Swiss Patent 439,858) | >1000 | |
| 2-3,4-dichlorophenylimino)-3-methyl-thiazoline-HCl (Swiss Patent 439,858) | >1000 | >1000 |
| 2-(4-chlorophenylimino)-3-methylthiazoline-HCl (Swiss Patent 439,858) | >1000 | >1000 |
| 1-naphthyl-N-methylcarbamate ("Sevin"; U.S. Pat. No. 2,903,478) | 1000 | >1000 |
| empir. C$_{10}$H$_{10}$Cl$_8$ ("Toxaphen"; U.S. Pat. No. 2,565,471) | 1000 | 1000 |

EXAMPLE 4

Test of the action against ticks: knock-down action against various development stages.

The test organisms are about 50 larvae, about 25 nymphs or about 10 imagines of each of the tick species Amblyomma hebraeum and Rhipicephalus bursa. The test organisms are dipped for a short time into aqueous emulsions or solutions having a specific concentration of the salts of the substances to be examined. The emulsions or solutions, which are contained in small test tubes, are then absorbed by cottonwool and the wetted test animals are left in the contaminated small tubes. The larvae are evaluated after 3 days and the nymphs and imagines after 14 days. The minimum substance concentration which effects 100% kill (LC$_{100}$) is determined, expressed in ppm of active substance based on the total of emulsion or solution.

| | Results LC$_{100}$ | | | |
|---|---|---|---|---|
| | A. hebraeum | | R. bursa | |
| Compound | nymphs | larvae | imagines | larvae |
| (1) 2-(2',3'-dimethyl-anilinomethyl)-2-imidazoline-hydrochloride | 1 | 1 | 50 | 1 |
| (2) 2-(2',3'-dichloroanilino-methyl)-2-imidazoline-hydrochloride | 1 | 1 | 100 | 1 |
| Comparison | | | | |
| 2-(3,4-dichlorophenyl-imino)-N-n-butylpyrrolidine ("Bimarit") | 100 | 100 | 100 | 10 |
| 1-naphthyl-N-methyl-carba- | | | | |

| | Results LC$_{100}$ | | | |
|---|---|---|---|---|
| | A. hebraeum | | R. bursa | |
| Compound | nymphs | larvae | imagines | larvae |
| mate ("Sevin":U.S. Pat. No. 2,903,478) | 10 | 5 | 100 | 10 |

The compounds of the formula I are used as compositions of the invention together with suitable carriers and/or adjuvants. Suitable carriers and adjuvants can be solid or liquid and are the substances conventionally used in the art of formulation, for example natural or regenerated substances, solvents, despersing agents, wetting agents, adhesives, thickeners and binders.

For application, the compounds of the formula I can be processed to dusts, emulsifiable concentrates, granules, dispersions, sprays, or to solutions or suspensions, in the conventional formulation which is commonly employed in application technology.

The compositions of the present invention are prepared in a manner known per se by homogeneously mixing and/or grinding the active ingredients of the formula I with suitable carriers, with or without the addition of despersing agents and solvents which are inert to the active ingredients. The active ingredients may be processed to the following formulations:

Solid formulations: dusts, tracking powders and granules (coated granules, impregnated granules and homogeneous granules);

Liquid formulations:
(a) active ingredient concentrates which are dispersible in water: wettable powders, pastes and emulsions;
(b) solutions: pour-on.

The content of active ingredient in the above described formulations is preferably between 1 and 80%.

EXAMPLE 5

Emulsifiable concentrate 20 parts by weight of a compound of the formula I are dissolved in 70 parts by weight of xylene and to this solution are added 10 parts by weight of an emulsifier consisting of a mixture of arylphenyl polyglycol ether and the calcium salt of dodecylbenzenesulfonic acid. The emulsifiable concentrate can be diluted with water in any ratio to form a milky emulsion.

EXAMPLE 6

Emulsifiable concentrate

With stirring, 5 to not more than 30 parts by weight of a compound of the formula I are dissolved at room temperature in 30 parts by weight of dibutyl phthalate, 10 parts by weight of Solvent 200 (high-aromatic mineral oil distillate of low viscosity) and 15 to 35 parts by weight of Dutrex 238 FC (viscous high-aromatic mineral oil distillate). Then 10 parts by weight of an emulsifier mixture consisting of castor oil polyglycol ether and the calcium salt of dodecylbenzenesulfonic acid are added. The resulting emulsifiable concentrate gives milky emulsions in water.

EXAMPLE 7

Wettable powder 5 to 30 parts by weight of a compound of the formula I are mixed intensively, in a mixing apparatus, with 5 parts by weight of an absorbent carrier (silica K 320 or Wessalon S) and 55 to 80 parts by weight of a carrier (bolus alba or kaolin B 24) and a mixture of dispersing agents consisting of 5 parts by weight of a Na laurylsulfonate and 5 parts by weight of an alkylaryl polyglycol ether. This mixture is ground to 5–15 μm in a pin mill or air jet mill. The resulting wettable powder gives a good suspension in water.

EXAMPLE 8

Dust 5 parts by weight of a compound of the formula I (powder) are mixed intensively with 2 parts by weight of precipitated silica and 93 parts by weight of talc.

EXAMPLE 9

Pour-on solution

| Compound of the formula I | 30.0 g |
|---|---|
| sodium dioctylsulfosuccinate | 3.0 g |
| benzyl alcohol | 48.0 g |
| groundnut oil | 19.8 g |
| | 100.8 g = 100 ml |

The active substance is dissolved in benzyl alcohol with stirring and if necessary also with gentle warming. The sodium dioctylsulfosuccinate and the groundnut oil are added to the solution and dissolved, with warming and thorough mixing.

EXAMPLE 10

Pour-on solution

| Compound of the formula I | 30.00 g |
|---|---|
| sodium dioctylsulfosuccinate | 3.00 g |
| benzyl alcohol | 35.46 g |
| ethylene glycol monomethyl ether | 35.46 g |
| | 103.92 g = 100 ml |

The active substance is dissolved in the bulk of the mixture of the two solvents with vigorous stirring. The sodium dioctylsulfosuccinate is then dissolved, with warming if necessary, and finally the solution is bulked with the remainder of the solvent mixture.

What is claimed is:

1. A method for controlling pests selected from the group consisting of mites and ticks which comprises applying thereto a pesticidally effective amount of a compound of the formula

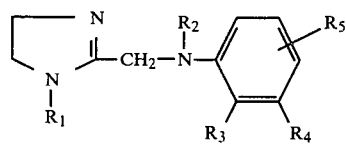

wherein
 each of $R_1$ and $R_2$ represents hydrogen or alkyl of from 1 to 10 carbon atoms,
 each of $R_3$ and $R_4$ represents alkyl of from 1 to 5 carbon atoms or halogen, and
 $R_5$ represents hydrogen, alkyl of from 1 to 5 carbon atoms or halogen,
or an acid addition salt thereof.

2. A method according to claim 1 in which each of $R_3$ and $R_4$ represents alkyl of from 1 to 5 carbon atoms or chlorine.

3. The method according to claim 2 in which the compound is 2-(2',3'-dimethylanilinomethyl)-2-imidazoline hydrochloride.

4. The method according to claim 2 in which the compound is 2-(2',3'-dichloroanilinomethyl)-2-imidazoline hydrochloride.

* * * * *